(12) United States Patent
Min et al.

(10) Patent No.: US 12,371,418 B2
(45) Date of Patent: Jul. 29, 2025

(54) PROCESS FOR PREPARING PYRIMIDINYL BIPYRIDINE COMPOUND AND INTERMEDIATE THEREFOR

(71) Applicant: BEYONDBIO INC., Daejeon (KR)

(72) Inventors: Changhee Min, Daejeon (KR); Ki-Hyun Nah, Cheongju-si (KR); Hoon Young Son, Daejeon (KR)

(73) Assignee: BEYONDBIO INC., Daejeon (KR)

( * ) Notice: Subject to any disclaimer, the term of this patent is extended or adjusted under 35 U.S.C. 154(b) by 715 days.

(21) Appl. No.: 17/640,715

(22) PCT Filed: Sep. 4, 2020

(86) PCT No.: PCT/KR2020/011996
§ 371 (c)(1),
(2) Date: Mar. 4, 2022

(87) PCT Pub. No.: WO2021/045585
PCT Pub. Date: Mar. 11, 2021

(65) Prior Publication Data
US 2022/0324839 A1 Oct. 13, 2022

(30) Foreign Application Priority Data
Sep. 6, 2019 (KR) .......................... 10-2019-0110734

(51) Int. Cl.
*C07D 401/14* (2006.01)
*A61P 25/28* (2006.01)
*A61P 35/00* (2006.01)
*C07D 401/06* (2006.01)

(52) U.S. Cl.
CPC .................. *C07D 401/14* (2013.01)

(58) Field of Classification Search
CPC ............................. C07D 401/14; C07D 401/06
See application file for complete search history.

(56) References Cited

FOREIGN PATENT DOCUMENTS

| | | |
|---|---|---|
| CN | 107250130 A | 10/2017 |
| EP | 3 255 042 A2 | 12/2017 |
| JP | 2018-504449 A | 2/2018 |
| KR | 10-2004-0026657 A | 3/2004 |
| KR | 10-2016-0096033 A | 8/2016 |
| KR | 10-1783642 B1 | 10/2017 |
| WO | 2004/084824 A2 | 10/2004 |
| WO | WO-2016126085 A2 * | 8/2016 ........... A61K 31/444 |
| WO | 2018/136700 A1 | 7/2018 |
| WO | 2019/032458 A1 | 2/2019 |

OTHER PUBLICATIONS

Korsager "Direct Route to 1,3-Diketones by Palladium-Catalyzed CarbonylativeCoupling of Aryl Halides with Acetylacetone" Chem. Eur. J. 2013, 19, 17687-91 (Year: 2013).*
Machine translation of WO 2016126085 by Google Patents (Year: 2016).*
International Search Report for PCT/KR2020/011996 dated Dec. 17, 2020 [PCT/ISA/210].
Written Opinion for PCT/KR2020/011996 dated Dec. 17, 2020 [PCT/ISA/237].
Office Action issued Apr. 18, 2023 in Japanese Application No. 2022-514845.
Extended European Search Report dated Aug. 8, 2023 from the European Patent Office in Application No. 20861078.2.

* cited by examiner

*Primary Examiner* — Amy L Clark
*Assistant Examiner* — John Josiah Macalipay Lopp
(74) *Attorney, Agent, or Firm* — Sughrue Mion, PLLC

(57) ABSTRACT

Provided are a process for preparing a pyrimidinyl bipyridine compound having high purity with high yields without using high-cost silica gels, and an intermediate used therein.

9 Claims, No Drawings

PROCESS FOR PREPARING PYRIMIDINYL BIPYRIDINE COMPOUND AND INTERMEDIATE THEREFOR

CROSS REFERENCE TO RELATED APPLICATIONS

This application is a National Stage of International Application No. PCT/KR2020/011996 filed Sep. 4, 2020, claiming priority based on Korean Patent Application No. 10-2019-0110734 filed Sep. 6, 2019.

Technical Field

The present invention relates to a process for preparing a pyrimidinyl bipyridine compound and an intermediate therefor. More particularly, the present invention relates to a process for preparing a pyrimidinyl bipyridine compound having high purity with high yields without using high-cost silica gels, and an intermediate used therein.

Background Art

The pyrimidinyl bipyridine compound represented by the following formula (1) is a cyclin-dependent kinase (CDK) inhibitor, which is known to be effective in the treatment of cancers such as colon cancer, lung cancer, glioma, and degenerative brain diseases such as Alzheimer's disease [Korean Patent No. 10-1783642].

(1)

Korean Patent No. 10-1783642 discloses a process for preparing the pyrimidinyl bipyridine compound of formula (1) by reacting the diketone compound of the following formula (2) with guanidine carbonate to obtain a pyrimidinyl pyridine compound, and subjecting it to Suzuki reaction with the dioxaborolane compound of the following formula (3), followed by O-demethylation, as shown in the following reaction scheme 1.

[Reaction Scheme 1]

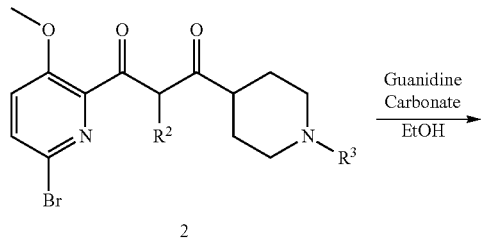

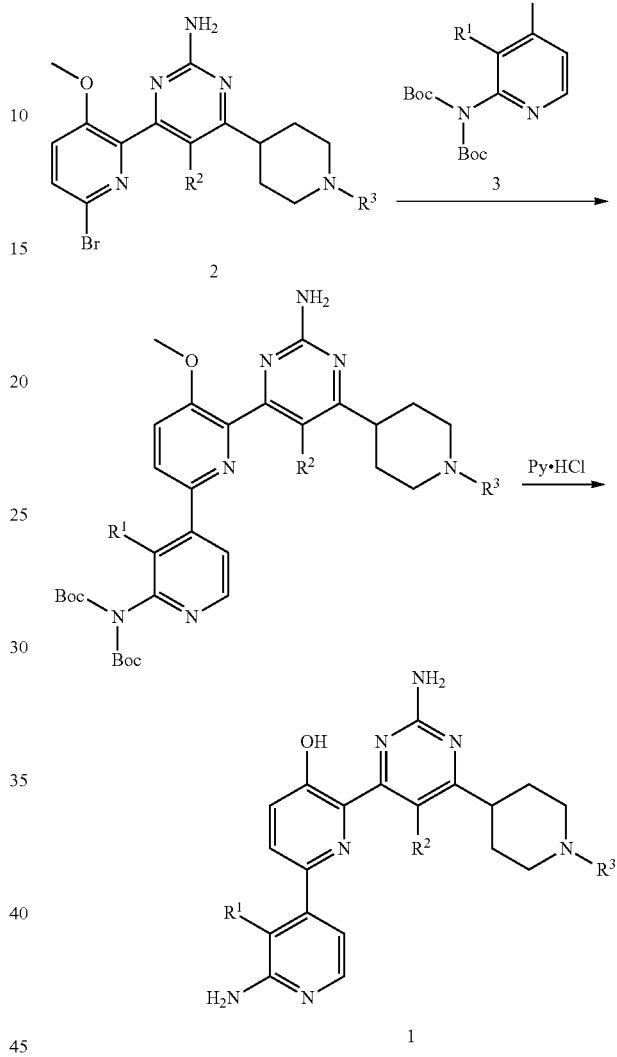

However, the above process has problems that the intermediate, pyrimidinyl pyridine compound has low solubility in organic solvents, so that the yield is significantly lowered during work-up and silica gel column purification processes, and impurities are generated in the O-demethylation process, resulting in lowering the purity.

DISCLOSURE

Technical Problem

The present inventors have studied diligently to solve the above problems in the preparation of the pyrimidinyl bipyridine compound represented by formula (1), and as a result, found out that, in the case that the diketone compound of formula (2) is subjected to Suzuki reaction with the dioxaborolane compound of formula (3), an intermediate having high solubility is generated and a separate O-demethylation process can be omitted. The present invention has been completed therethrough.

Therefore, an object of the present invention is to provide a process for preparing a pyrimidinyl bipyridine compound having high purity with high yields without using high-cost silica gels.

Another object of the present invention is to provide an intermediate used in the preparation process.

Technical Solution

One embodiment of the present invention relates to a process for preparing a pyrimidinyl bipyridine compound of the following formula (1), comprising the steps of:
(i) subjecting a compound of the following formula (2) to Suzuki reaction with a compound of the following formula (3) to obtain a compound of the following formula (4);
(ii) deprotecting the compound of the following formula (4) to obtain a compound of the following formula (5); and
(iii) reacting the compound of the following formula (5) with a guanidine compound:

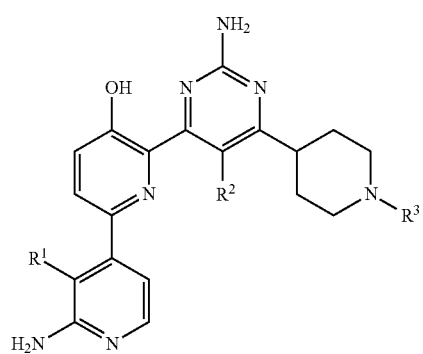

(1)

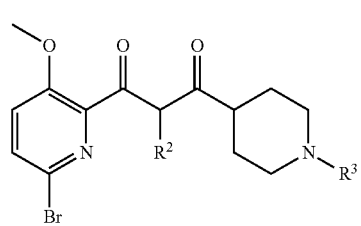

(2)

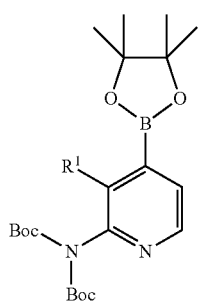

(3)

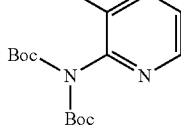

(4)

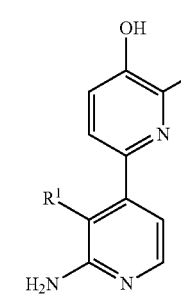

(5)

wherein,
$R^1$ is halogen,
$R^2$ is hydrogen or a $C_1$-$C_6$ alkyl group, and
$R^3$ is a $C_1$-$C_6$ alkyl group.

The term "$C_1$-$C_6$ alkyl group" as used herein means a linear or branched hydrocarbon having 1 to 6 carbon atoms, which includes methyl, ethyl, n-propyl, i-propyl, n-butyl, i-butyl, n-pentyl, i-pentyl, n-hexyl and the like, but is not limited thereto.

Hereinafter, the preparation process of the present invention is described in more detail referring to the following reaction scheme 2. The process depicted in the following reaction scheme 2 represents merely a typical example, and various changes may be made to reagents and reaction conditions without limitation.

[Reaction Scheme 2]

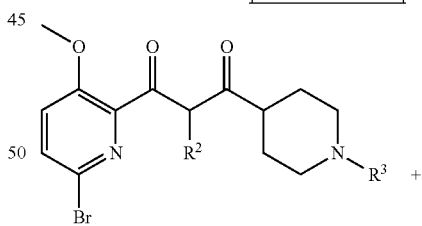

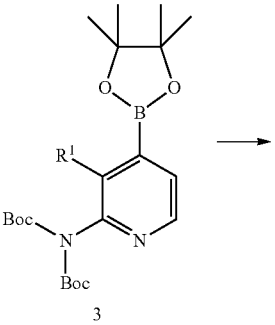

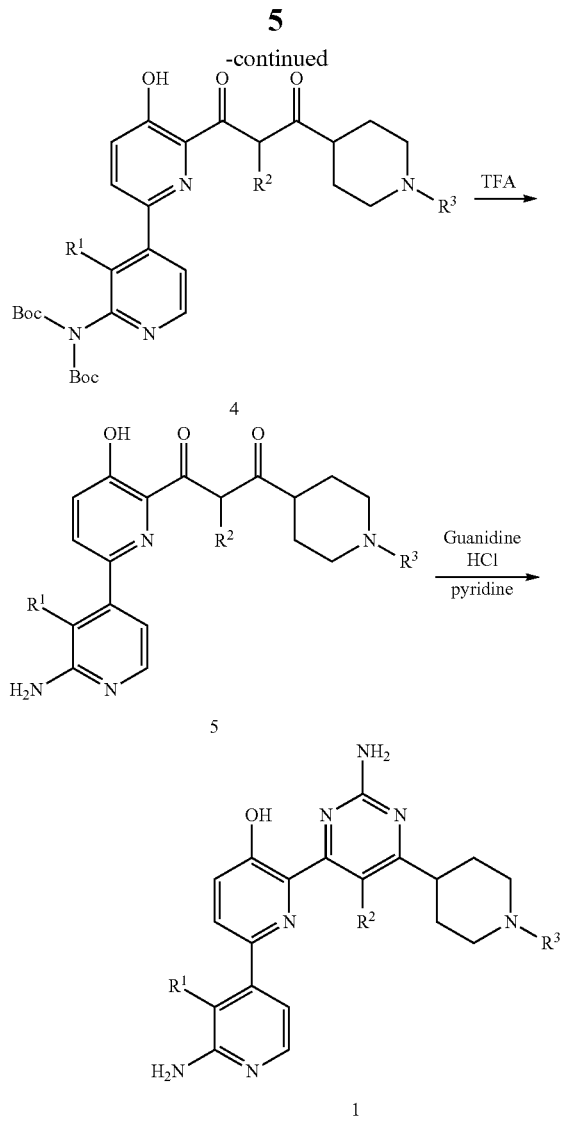

Step 1: Synthesis of Compound of Formula (4)

The compound of formula (4) can be obtained by subjecting the compound of formula (2) to Suzuki reaction with the compound of formula (3).

The Suzuki reaction may be carried out in the presence of a palladium catalyst and a base.

As the palladium catalyst, tetrakis(triphenylphosphine)palladium(0) (Pd(PPh$_3$)$_4$), (1,1'-bis(diphenylphosphino)ferrocene)palladium(II)dichloride (PdCl$_2$(dppf)$_2$) and the like may be used, and as the base, potassium phosphate (K$_3$PO$_4$), potassium carbonate (K$_2$CO$_3$) and the like may be used.

As the reaction solvent, a mixed solvent of tetrahydrofuran and water may be preferably used, and reflux condition is suitable for the reaction temperature.

Step 2: Synthesis of Compound of Formula (5)

The compound of formula (5) can be obtained by deprotecting the compound of formula (4).

The deprotection may be carried out in the presence of an acid.

As the acid, trifluoroacetic acid (TFA), hydrochloric acid (c-HCl) and the like can be used.

As the reaction solvent, dichloromethane, tetrahydrofuran, acetonitrile and the like may be preferred, and the suitable temperature for the reaction may be −20° C. to room temperature.

Step 3: Synthesis of Compound of Formula (1)

The compound of formula (1) can be obtained by reacting the compound of formula (5) with a guanidine compound.

The guanidine compound may be guanidine HCl, guanidine carbonate and the like.

The reaction may be carried out in the presence of a base in pyridine solvent.

As the base, potassium carbonate (K$_2$CO$_3$), cesium carbonate (Cs$_2$CO$_3$) and the like may be used.

In the reaction, reflux condition is suitable for the reaction temperature.

The compound of formula (1) prepared as above can be purified with acetone and ethanol to obtain the compound having a purity of 99% or higher.

One embodiment of the present invention relates to a process for preparing a pharmaceutically acceptable salt of the compound of formula (1) by reacting the compound of formula (1) prepared by the above preparation process with an acid.

As the acid, non-toxic inorganic and organic acids may be used, and examples thereof may include hydrochloric acid, phosphoric acid, sulfuric acid, nitric acid, tartaric acid, methanesulfonic acid, p-toluenesulfonic acid, acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, malic acid, malonic acid and the like. Particularly, hydrochloric acid is preferred.

As the reaction solvent, methanol, 1,4-dioxane and the like are preferred, and the suitable reaction temperature is room temperature.

The pharmaceutically acceptable salt of the compound of formula (1) prepared as above can be recrystallized with water and acetone to obtain the compound having a purity of 99% or higher.

One embodiment of the present invention relates to a compound of formula (4) or a compound of formula (5) which is an intermediate for preparing the compound of formula (1):

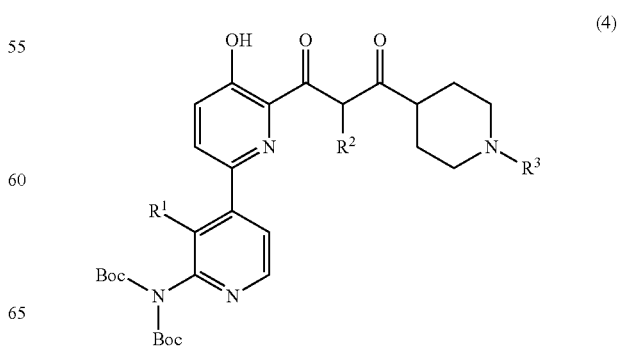

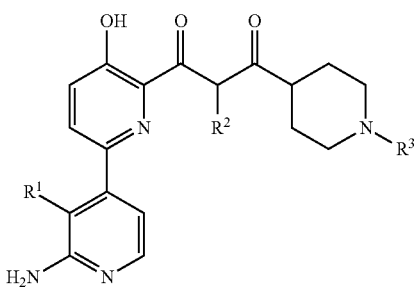

(5)

wherein,
R¹ is halogen,
R² is hydrogen or a $C_1$-$C_6$ alkyl group, and
R³ is a $C_1$-$C_6$ alkyl group.

In one embodiment of the present invention, R¹ is fluorine, R² is methyl group, and R³ is i-propyl group.

Advantageous Effects

In accordance with the preparation process of the present invention, by using the intermediate of formula (4) having excellent solubility thereby facilitating work-up and purification, the pyrimidinyl bipyridine compound of formula (1) having high purity can be mass-produced with high yields without using high-cost silica gels.

BEST MODE

Hereinafter, the present invention will be described in more detail by the following examples. It will be obvious to those skilled in the art that these examples are merely described for illustration of the present invention and the scope of the present invention is not limited thereto.

Preparation Example 1: Preparation of 2-[3-fluoro-4-(4,4,5,5-tetramethyl-[1,3,2]dioxaborolan-2-yl)-2-pyridinyl]-imidodicarbonic acid-1,3-bis(1,1-dimethylethyl) ester

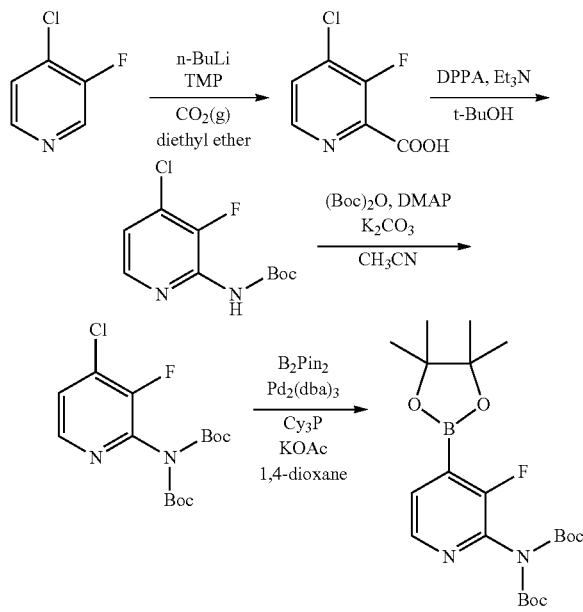

Preparation Example 1-1: Preparation of 4-chloro-3-fluoro-pyridine-2-carboxylic acid The inside of the reactor was filled with nitrogen, and 2.5M n-butyllithium hexane solution (n-BuLi (2.5M in Hexane)) (502 mL, 1.254 mol) was added to diethylether at −78° C. 2,2,6,6-Tetramethylpiperidine (TMP) (213 mL, 1.254 mol) was added dropwise thereto, followed by stirring for 1 hour. 4-Chloro-3-fluoropyridine (150 g, 1.140 mol) was slowly added dropwise and stirred at −78° C. for 1 hour. The resulting reaction solution was slowly added dropwise to a reactor having diethyl ether with a large number of crushed dry ice. After the dropwise addition, the temperature was slowly raised to room temperature, and the reaction solution was concentrated. A 2N hydrochloric acid aqueous solution was slowly added to form a solid, followed by stirring for 30 minutes and filtration. The solid was washed with water, and n-hexane was added to the filtered solid compound, followed by stirring for 30 minutes and filtration. After washing with n-hexane, the solid compound was dried in a dryer at 65° C. for 16 hours. The dried compound was purified with n-hexane/diethyl ether and dried to obtain the white title compound (150 g, 75%).

$^1$H NMR (600 MHz, DMSO-$d_6$) δ 8.45 (d, J=5.4 Hz, 1H), 7.93 (t, J=5.4 Hz, 1H)

Preparation Example 1-2: Preparation of (4-chloro-3-fluoro-pyridin-2-yl)-carbamic acid-tert-butyl ester To a reactor were added 4-chloro-3-fluoro-pyridine-2-carboxylic acid (1.23 kg, 7.007 mol) and tert-butanol. Triethylamine (2.3 L, 16.116 mol) was added thereto, and diphenylphosphoryl azide (DPPA) (2.3 L, 10.511 mol) was added, followed by raising the temperature. The reaction was performed under reflux condition for 16 hours, and then the temperature was lowered to room temperature, followed by concentration under reduced pressure. 1N hydrochloric acid aqueous solution and ethyl acetate were added thereto, followed by stirring for 1 hour. The organic layer was separated, and pH was neutralized with saturated sodium hydrogen carbonate aqueous solution. The organic layer was separated, and magnesium sulfate ($MgSO_4$) and activated carbon were added thereto, followed by stirring for 1 hour to improve the moisture and color of the organic layer. It was filtered with celite, washed with ethyl acetate, and concentrated under reduced pressure to obtain the light brown title compound (1.73 kg, Quant.).

$^1$H NMR (600 MHz $CDCl_3$) δ 8.11 (d, J=4.8 Hz, 1H), 7.09 (br, 1H), 7.08 (t, J=4.8 Hz, 1H), 1.52 (s, 9H)

Preparation Example 1-3: Preparation of 2-(3-fluoro-4-chloropyridinyl)-imidocarbonic acid-1,3-bis(1,1-dimethylethyl)ester (4-Chloro-3-fluoro-pyridin-2-yl)-carbamic acid-tert-butyl ester (1.723 kg, 6.987 mol) was dissolved in acetonitrile, and di-tert-butyl dicarbonate (($Boc)_2O$) (3.05 kg, 13.784 mol) and potassium carbonate ($K_2CO_3$) (2.9 kg, 20.961 mol) were added thereto and stirred. After slowly adding 4-dimethylaminopyridine (85 g, 0.699 mol), the resulting mixture was stirred at room temperature for 16 hours. After filtration with celite, it was washed with ethyl acetate and concentrated under reduced pressure. 1N hydrochloric acid aqueous solution and ethyl acetate were added and stirred for 1 hour, and then the organic layer was separated. A saturated sodium hydrogen carbonate aqueous solution was added to the organic layer to adjust pH to 8 and stirred for 1 hour. The organic layer was separated, and magnesium sulfate (MgSO$_4$) and activated carbon were added to improve the moisture and color of the organic layer. After filtration with celite, it was washed with ethyl acetate and concentrated under reduced pressure. After adding n-hexane/diethyl ether, the resulting mixture was cooled to 0~4° C. and stirred for recrystallization. The resulting solid was filtered, washed with n-hexane and dried to obtain the light brown title compound (1.46 kg, 60%).

$^1$H NMR (600 MHz CDCl$_3$) δ 8.20 (d, J=5.4 Hz, 1H), 7.36 (t, J=4.8 Hz, 1H), 1.43 (s, 18H)

Preparation Example 1-4: Preparation of 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester 2-(3-Fluoro-4-chloropyridinyl)-imidocarbonic acid-1,3-bis(1,1-dimethylethyl)ester (150 g, 0.433 mol) was dissolved in 1,4-dioxane. Then, bis(pinacolato)diboron (241 g, 0.952 mol), tris(dibenzylideneacetone)dipalladium (19.8 g, 0.0216 mol), tricyclohexylphosphine (9.0 g, 0.0344 mol), and potassium acetate (170 g, 1.730 mol) were added, followed by stirring under reflux for 16 hours. After the reaction was completed, it was cooled to room temperature, and celite and dichloromethane were added to the reactor, followed by stirring for 30 minutes. It was filtered with celite to remove the solid residue and washed with dichloromethane. The filtrate was concentrated under reduced pressure, dichloromethane was added, sodium hydrogen carbonate aqueous solution was added, and the resulting mixture was stirred for 30 minutes. At this time, the pH of the water layer should be basic. The organic layer was separated, and magnesium sulfate (MgSO$_4$) and activated carbon were added to improve the moisture and color of the organic layer. After filtration with celite, it was washed with dichloromethane and concentrated under reduced pressure. Then, n-hexane was added and recrystallization was performed to obtain the white title compound (133 g, 70%).

$^1$H NMR (600 MHz CDCl$_3$) δ 8.29 (d, J=4.8 Hz, 1H), 7.57 (t, J=4.8 Hz, 1H), 1.39 (s, 18H), 1.34 (s, 12H)

Preparation Example 2: Preparation of methyl 6-bromo-3-methoxypicolinate

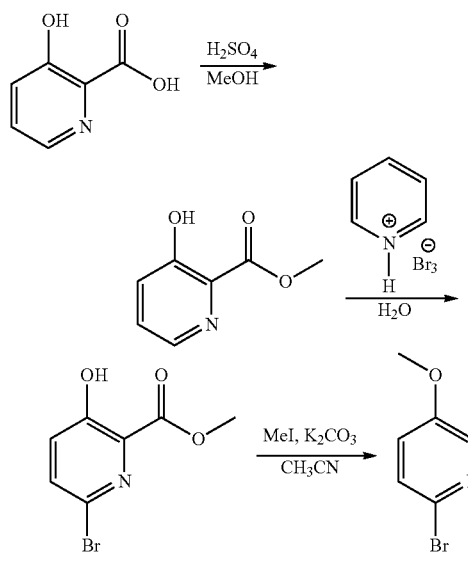

Preparation Example 2-1: Preparation of methyl 3-hydroxypicolinate

After 3-hydroxypicolinic acid (2.4 kg, 17.32 mol) was added to methanol, sulfuric acid (2.4 L) was slowly added dropwise at 0° C. and stirred under reflux for 24 hours. After cooling to room temperature, it was concentrated under reduced pressure. After adding water and cooling to 0° C., pH was adjusted to 7~8 using 6N sodium hydroxide aqueous solution. After extraction with ethyl acetate, magnesium sulfate (MgSO$_4$) was added, and the organic layer was dried and concentrated under reduced pressure. Then, n-hexane was added, and recrystallization was performed to obtain the off-white title compound (2.0 kg, 75%).

$^1$H NMR (600 MHz, CDCl$_3$) δ 10.63 (s, 1H), 8.28 (s, 1H), 7.41 (t, J=1.8 Hz, 1H), 7.37 (d, J=1.8 Hz, 1H), 4.06 (s, 3H)

Preparation Example 2-2: Preparation of methyl 6-bromo-3-hydroxypicolinate

Methyl 3-hydroxypicolinate (1.2 kg, 7.833 mol) was dissolved in distilled water (30 L), and then pyridinium tribromide (3.24 kg, 10.185 mol) was slowly added dropwise thereto. After completion of the addition, the resulting mixture was stirred at room temperature for 24 hours. The resulting solid was filtered and washed with water thoroughly. The filtered solid was dissolved in dichloromethane, the organic layer was separated, and magnesium sulfate (MgSO$_4$) was added. The organic layer was dried, concentrated under reduced pressure, and vacuum-dried to obtain the off-white title compound (1.46 kg, 80%).

$^1$H NMR (600 MHz CDCl$_3$) δ 10.69 (s, 1H), 7.56 (d, J=8.4 Hz, 1H), 7.27 (d, J=8.4 Hz, 1H), 4.06 (s, 3H)

Preparation Example 2-3: Preparation of methyl 6-bromo-3-methoxypicolinate

Methyl 6-bromo-3-hydroxypicolinate (230 g, 0.9912 mol) was added to acetonitrile. Potassium carbonate (274 g, 1.9825 mol) and methane iodide (123 mL, 1.9825 mol) were added thereto, and the temperature was raised. After stirring under reflux condition for 16 hours and cooling to room temperature, it was filtered with celite. After washing with ethyl acetate, the filtrate was concentrated under reduced pressure. The organic layer was extracted from the concentrate using water and dichloromethane and separated, and magnesium sulfate (MgSO$_4$) was added. The organic layer was dried and concentrated under reduced pressure. The concentrate was recrystallized with n-hexane/diethyl ether and washed with n-hexane to obtain the off-white title compound (190 g, 78%).

$^1$H NMR (600 MHz CDCl$_3$) δ 10.69 (s, 1H), 7.57 (d, J=8.4 Hz, 1H), 7.26 (d, J=8.4 Hz, 1H), 3.95 (s, 3H), 3.91 (s, 3H)

Preparation Example 3: Preparation of 1-(1-isopropylpiperidin-4-yl)propan-1-one

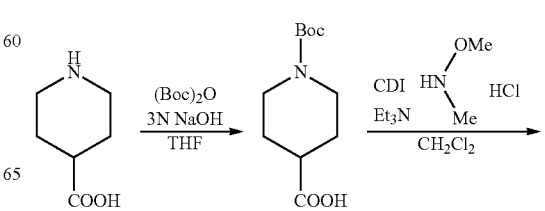

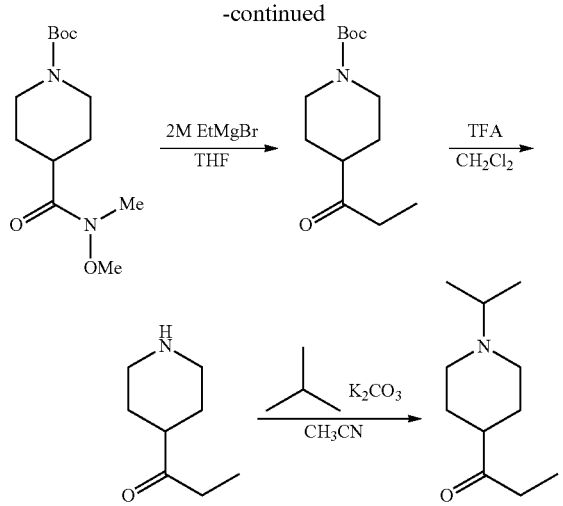

Preparation Example 3-1: Preparation of 1-(tert-butoxycarbonyl)piperidine-4-carboxylic acid 4-Piperidinecarboxylic acid (70.0 g, 0.542 mol) was dissolved in tetrahydrofuran (THF), and then di-tert-butyl dicarbonate ((Boc)₂O) (236.6 g, 1.084 mol) and 3N sodium hydroxide aqueous solution were added. After stirring at room temperature for 16 hours, completion of the reaction was confirmed, and the reaction solution was concentrated under reduced pressure. 3N hydrochloric acid aqueous solution was added to the concentrate to adjust pH to 7~8. Dichloromethane was added and the organic layer was separated. The separated organic layer was dried over magnesium sulfate (MgSO₄) and filtered. After the filtrate was concentrated under reduced pressure, n-hexane was added for recrystallization to obtain the white title compound (121.8 g, 98.0%).

$^1$H NMR (600 MHz, CDCl₃) δ 4.02 (br, 2H), 2.86 (br, 2H), 2.48 (m, 1H), 1.91 (br, 2H), 1.63 (m, 2H), 1.45 (s, 9H)

Preparation Example 3-2: Preparation of tert-butyl-4-(methoxy(methyl)carbamoyl)piperidine-1-carboxylate After dissolving 1-(tert-butoxycarbonyl)piperidine-4-carboxylic acid (118 g, 0.515 mol) in dichloromethane, 1,1'-carbonyldiimidazole (CDI) (108.6 g, 0.669 mol) was added. After the addition was completed, the resulting mixture was stirred at room temperature for 1~2 hours. N,O-dimethylhydroxylamine hydrochloride (65.3 g, 0.669 mol) and triethylamine (Et₃N) (67.7 g, 0.669 mol) were added and stirred at room temperature for 16 hours. After confirming completion of the reaction, saturated ammonium chloride (Sat. NH₄Cl) was added, and the organic layer was separated. To the separated organic layer was added 2N hydrochloric acid aqueous solution, followed by separation of the organic layer. Saturated sodium chloride (Brine) was added to the separated organic layer and the organic layer was separated. The separated organic layer was dried over magnesium sulfate (MgSO₄) and filtered. The filtrate was concentrated under reduced pressure to obtain the white title compound (137.8 g, 95.3%).

$^1$H NMR (600 MHz, CDCl₃) δ 4.12 (br, 2H), 3.71 (s, 3H), 3.18 (s, 3H), 2.79 (br, 3H), 1.63 (m, 4H), 1.46 (s, 9H)

Preparation Example 3-3: Preparation of tert-butyl 4-propionyl piperidine-1-carboxylate tert-Butyl-4-(methoxy(methyl)carbamoyl)piperidine-1-carboxylate (132 g, 0.485 mol) was dissolved in tetrahydrofuran (THF), and then the temperature was lowered to 4~10° C. 2M ethylmagnesium bromide (2M EtMgBr) (727 mL, 1.454 mol) was slowly added and stirred for 30 minutes, followed by stirring at room temperature for 16 hours. After confirming completion of the reaction, it was cooled to 4~10° C., and water was slowly added thereto. 2N hydrochloric acid aqueous solution was added, and the organic layer was separated. The separated organic layer was dried over magnesium sulfate (MgSO₄) and filtered. The filtrate was concentrated under reduced pressure to obtain the yellow title compound (109 g, 93%).

$^1$H NMR (600 MHz, CDCl₃) δ 4.11 (br s, 2H), 2.77 (s, 2H), 2.52-2.42 (m, 3H), 1.79 (br s, 2H), 1.58-1.48 (m, 2H), 1.45 (s, 9H), 1.05 (t, J=7.2 Hz, 3H)

Preparation Example 3-4: Preparation of 1-(piperidin-4-yl)propan-1-one tert-Butyl 4-propionyl piperidine-1-carboxylate (130 g, 0.539 mol) was dissolved in dichloromethane, and trifluoroacetic acid (TFA) (301 mL, 3.932 mol) was slowly added, followed by stirring at room temperature for 16 hours. After confirming completion of the reaction, the reaction solution was concentrated under reduced pressure. To the concentrate were added 3N sodium hydroxide aqueous solution and dichloromethane, and the organic layer was separated. The separated organic layer was dried over magnesium sulfate (MgSO₄) and filtered. The filtrate was concentrated under reduced pressure to obtain the brown title compound (68.4 g, 90%).

$^1$H NMR (600 MHz, CDCl₃) δ 3.12 (d, J=10.8 Hz 2H), 2.63 (t, J=12 Hz, 2H), 2.48-2.42 (m, 3H), 1.80 (d, J=13.2 Hz, 2H), 1.62 (s, 2H), 1.54-1.48 (m, 2H), 1.06-1.03 (m, 3H)

Preparation Example 3-5: Preparation of 1-(1-isopropylpiperidin-4-yl)propan-1-one 1-(Piperidin-4-yl)propan-1-one (76 g, 0.538 mol) was dissolved in acetonitrile, and then potassium carbonate (K₂CO₃) (223.1 g, 1.614 mol) and isopropyl iodide (137.2 g, 0.807 mol) were added. The temperature was raised, and the resulting mixture was stirred under reflux condition for 16 hours. After confirming completion of the reaction, the temperature was lowered to room temperature, followed by celite filtration. The filtrate was concentrated under reduced pressure, water and ethyl acetate were added, and the organic layer was separated. The separated organic layer was dried over magnesium sulfate (MgSO₄) and filtered. The filtrate was concentrated under reduced pressure and distilled under high pressure to obtain the colorless title compound (68.4 g, 90%).

$^1$H NMR (600 MHz, CDCl₃) δ 2.92-2.86 (m, 2H), 2.74-2.68 (m, 1H), 2.47 (q, J=7.2 Hz, 2H), 2.32-2.24 (m, 1H), 2.16 (t, J=11.4 Hz, 2H), 1.87 (d, J=13.2 Hz, 2H), 1.70-1.60 (m, 2H), 1.08-1.02 (m, 9H)

Preparation Example 4: Preparation of 1-(6-bromo-3-methoxypyridin-2-yl)-3-(1-isopropylpiperidin-4-yl)-2-methylpropane-1,3-dione (2a)

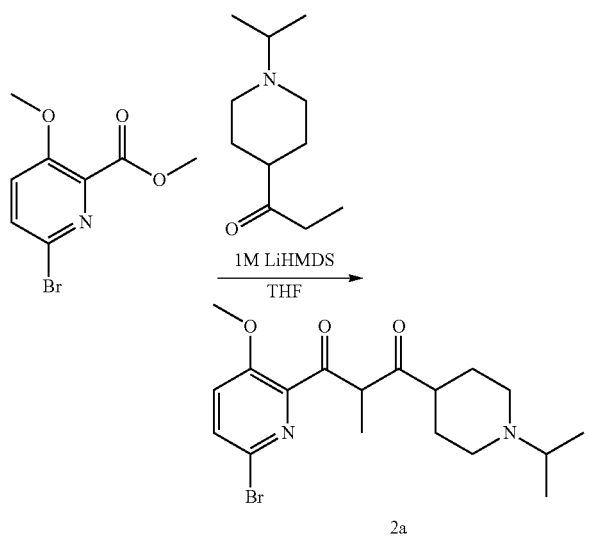

Methyl 6-bromo-3-methoxypicolinate (615.15 g, 2.50 mol) obtained from Preparation Example 2 was dissolved in tetrahydrofuran (THF), and then 1-(1-isopropylpiperidin-4-yl)propan-1-one (549.9 g, 3.00 mol) obtained from Preparation Example 3 was added. The temperature was lowered to −70~−78° C., and 1M lithium bis(trimethylsilyl)amide (1M LiHMDS) (5.00 L, 5.00 mol) was slowly added. After the addition was completed, the resulting mixture was stirred for 30 minutes, and the temperature was slowly raised to room temperature. After stirring at room temperature for 3 hours, when the content of methyl 6-bromo-3-methoxypicolinate was 5~7% by HPLC, saturated ammonium chloride (Sat. NH$_4$Cl) was slowly added to terminate the reaction. The organic layer was separated, and the separated organic layer was dried over magnesium sulfate (MgSO$_4$) and filtered. The filtrate was concentrated under reduced pressure to obtain the light brown title compound (537 g, yield 54%, purity >95%).

$^1$H NMR (600 MHz, CDCl$_3$) δ 7.54 (d, J=9 Hz, 1H), 7.27 (d, J=9 Hz, 1H), 4.82-4.70 (m, 1H), 3.92 (s, 3H), 2.94 (d, J=9 Hz, 2H), 2.85 (br s, 1H), 2.61 (br s, 1H), 2.40-2.22 (m, 2H), 2.10-1.90 (m, 2H), 1.80-1.60 (m, 4H), 1.35 (d, J=7.2 Hz, 3H), 1.05 (d, J=5.4 Hz, 6H)

Example 1: Preparation of 2'-amino-6-(2-amino-6-(1-isopropylpiperidin-4-yl)-5-methylpyrimidin-4-yl)-3'-fluoro-[2,4'-bipyridin]-5-ol (1a)

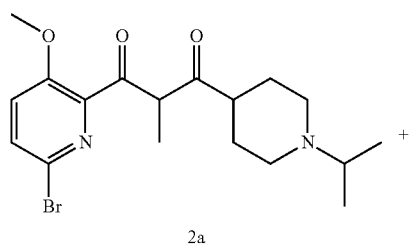

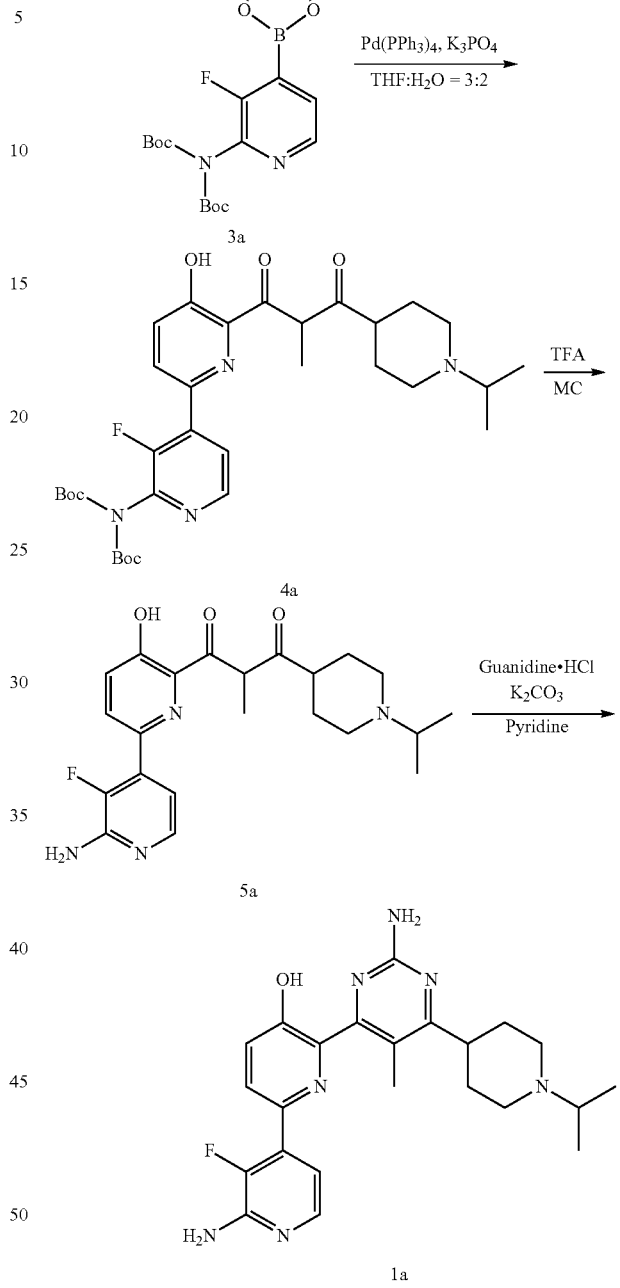

Example 1-1: Preparation of tert-Butyl (3'-fluoro-5-hydroxy-6-(3-(1-isopropylpiperidin-4-yl)-2-methyl-3-oxopropanoyl)-[2,4'-bipyridin]-2'-yl)dicarbamate (4a)

1-(6-Bromo-3-methoxypyridin-2-yl)-3-(1-isopropylpiperidin-4-yl)-2-methylpropane-1,3-dione (2a) (795 g, 2.00 mol) obtained from Preparation Example 4, 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester (1.23 kg, 2.80 mol) obtained from Preparation Example 1, tetrakis(triphenylphosphine) palladium(0) (Pd(PPh$_3$)$_4$)

(115.6 g, 0.10 mol) and potassium phosphate ($K_3PO_4$) (1.27 kg, 6.00 mol) were added to tetrahydrofuran/water (3/2). The temperature was raised, and the resulting mixture was stirred under reflux for 16 hours. After completion of the reaction, it was cooled to room temperature. After the organic layer was separated, saturated sodium chloride (NaCl) aqueous solution was added to the organic layer, and the organic layer was re-separated. The separated organic layer was dried over magnesium sulfate ($MgSO_4$) and filtered. The filtrate was concentrated under reduced pressure, and potassium phosphate ($K_3PO_4$) (1.27 kg, 6.00 mol) and tetrahydrofuran/water (3/2) were added to the concentrated solution. The temperature was raised, and the resulting mixture was stirred under reflux condition for 16 hours. After completion of the reaction, it was cooled to room temperature. The organic layer was separated, saturated sodium chloride (NaCl) aqueous solution was added to the organic layer, and the organic layer was re-separated. The separated organic layer was dried over magnesium sulfate ($MgSO_4$) and filtered. The filtrate was concentrated under reduced pressure to obtain the title compound (860 g, yield 70%, purity >95%).

$^1$H NMR (600 MHz, $CDCl_3$) δ 8.41 (d, J=5.4 Hz, 1H), 8.21 (t, J=5.4 Hz, 1H), 8.16 (d, J=7.8 Hz, 1H), 7.90 (d, J=7.8 Hz, 1H), 3.09-3.11 (m, 2H), 2.92-2.96 (m, 1H), 2.83-2.85 (m, 1H), 2.31-2.34 (m, 2H), 2.13-2.18 (m, 5H), 1.87-1.90 (m, 2H), 1.43 (s, 18H), 1.12 (d, J=6.6 Hz, 6H)

Example 1-2: Preparation of 1-(2'-amino-3'-fluoro-5-hydroxy-[2,4'-bipyridin]-6-yl)-3-(1-isopropylpiperidin-4-yl)-2-methylpropane-1,3-dione (5a)

tert-Butyl (3'-fluoro-5-hydroxy-6-(3-(1-isopropylpiperidin-4-yl)-2-methyl-3-oxopropanoyl)-[2,4'-bipyridin]-2'-yl) dicarbamate (4a) (20 g, 0.03 mol) was dissolved in dichloromethane, the temperature was lowered to −10~0° C., and trifluoroacetic acid (TFA) (37.4 mL, 0.49 mol) was slowly added. When the addition was completed, the resulting mixture was stirred at room temperature for 16 hours. After completion of the reaction, the reaction solution was concentrated under reduced pressure. To the concentrate were added water and ethyl acetate, and pH was adjusted to 12~14 with 2N sodium hydroxide aqueous solution. The resulting solid was filtered to obtain the brown title compound (9.4 g, yield 70%, purity >98%).

$^1$H NMR (600 MHz, DMSO-$d_6$) δ 8.23 (d, J=9 Hz, 1H), 8.11 (d, J=9 Hz, 1H), 7.84 (d, J=5.4 Hz, 1H), 6.96 (t, J=4.8 Hz, 1H), 6.40 (br s, 2H), 2.86-2.91 (m, 3H), 2.69-2.71 (m, 1H), 2.20-2.24 (m, 2H), 2.01 (s, 3H), 1.85-1.87 (m, 2H), 1.75-1.77 (m, 2H), 0.96 (d, J=6.6 Hz, 6H)

Example 1-3: Preparation of 2'-amino-6-(2-amino-6-(1-isopropylpiperidin-4-yl)-5-methylpyrimidin-4-yl)-3'-fluoro-[2,4'-bipyridin]-5-ol (1a)

1-(2'-amino-3'-fluoro-5-hydroxy-[2,4'-bipyridin]-6-yl)-3-(1-isopropylpiperidin-4-yl)-2-methylpropane-1,3-dione (5a) (100 g, 0.24 mol), guanidine HCl (230.48 g, 2.41 mol) and potassium carbonate ($K_2CO_3$) (666.91 g, 4.82 mol) were added to pyridine. The temperature was raised, and the resulting mixture was stirred under reflux condition for 24 hours. After completion of the reaction, the temperature was lowered to 50~60° C., followed by filtration. The filtrate was concentrated under reduced pressure and water was added thereto. After the temperature was lowered to −10~−5° C., pH was adjusted to 1~2 with 2N hydrochloric acid aqueous solution, and the pH was adjusted to 7~7.5 with 2N sodium hydroxide. The resulting solid was filtered, washed with water, and dried to obtain the title compound (105 g, yield 99.5%).

Then, to purify the title compound obtained above, purification process was performed with acetone and ethanol to obtain the title compound (80.7 g, yield 76.5%, purity >99%).

$^1$H NMR (600 MHz, DMSO-$d_6$) δ 7.79 (d, J=7.8 Hz, 1H), 7.77 (d, J=5.4 Hz, 1H), 7.46 (d, J=8.4 Hz, 1H), 6.98 (t, J=4.8 Hz, 1H), 6.61 (s, 2H), 6.27 (s, 2H), 2.95 (d, J=11.4 Hz, 2H), 2.92-2.86 (m, 1H), 2.84-2.76 (m, 1H), 2.35 (t, J=10.8 Hz, 2H), 2.25 (s, 3H), 1.90-1.80 (m, 2H), 1.70 (d, J=12.6 Hz, 2H), 1.03 (d, J=6.6 Hz, 6H)

Example 2: Preparation of 2'-amino-6-(2-amino-6-(1-isopropylpiperidin-4-yl)-5-methylpyrimidin-4-yl)-3'-fluoro-[2,4'-bipyridin]-5-ol trihydrochloride 2'-Amino-6-(2-amino-6-(1-isopropylpiperidin-4-yl)-5-methylpyrimidin-4-yl)-3'-fluoro-[2,4'-bipyridin]-5-ol (1a) (56 g, 0.13 mol) obtained from Example 1 was reacted with hydrochloric acid in methanol and stirred at room temperature for 24 hours. The reaction solution was concentrated under reduced pressure, and water was added to dissolve it. Acetone was slowly added to the dissolved solution to proceed with recrystallization. The resulting solid was filtered, washed with acetone, and dried. To completely remove the residual solvent of the dried solid compound, it was dissolved in water and recrystallized with acetone to obtain the title compound (63 g, yield 90%, purity >99%).

$^1$H NMR (600 MHz, DMSO-$d_6$) δ 8.41 (br s, 1H), 8.06-8.07 (m, 1H), 7.86-7.87 (m, 1H), 7.74 (m, 1H), 7.42 (m, 1H), 3.59-3.63 (m, 2H), 3.43-3.45 (m, 1H), 3.43 (m, 1H), 3.11-3.16 (m, 2H), 2.16-2.23 (m, 2H), 2.14 (s, 3H), 1.98-2.00 (m, 2H), 1.03 (d, J=6.6 Hz, 6H)

The invention claimed is:

1. A process for preparing a pyrimidinyl bipyridine compound of the following formula (1), which comprises the steps of:

(i) subjecting a compound of the following formula (2) to Suzuki reaction with a compound of the following formula (3) to obtain a compound of the following formula (4);

(ii) deprotecting the compound of the following formula (4) to obtain a compound of the following formula (5); and (iii) reacting the compound of the following formula (5) with a guanidine compound:

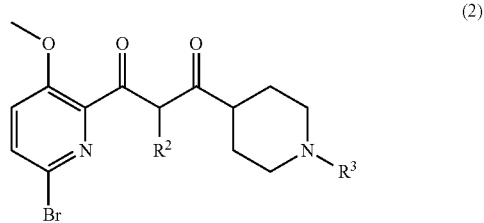

(2)

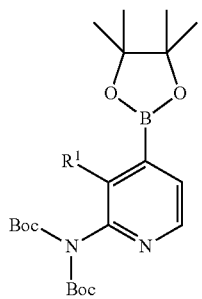

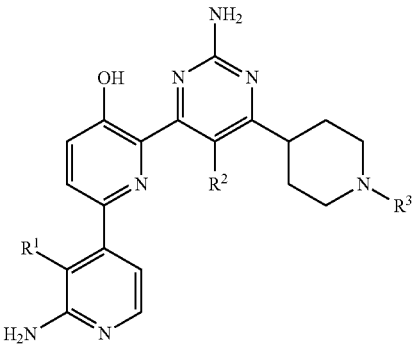

wherein,
R¹ is halogen,
R² is hydrogen or a $C_1$-$C_6$ alkyl group, and
R³ is a $C_1$-$C_6$ alkyl group.

2. The process according to claim 1, wherein the Suzuki reaction of the step (i) is carried out in the presence of tetrakis(triphenylphosphine)palladium(0) and potassium phosphate.

3. The process according to claim 1, wherein the deprotection of the step (ii) is carried out in the presence of trifluoroacetic acid.

4. The process according to claim 1, wherein the guanidine compound of the step (iii) is guanidine hydrochloride.

5. The process according to claim 1, wherein the reaction of the step (iii) is carried out in the presence of potassium carbonate in pyridine solvent.

6. The process according to claim 1, comprising the step of purifying the pyrimidinyl bipyridine compound of formula (1) obtained from the step (iii) with acetone and ethanol.

7. The process according to claim 1, comprising the further step of reacting the compound of formula (1) with an acid to form a pharmaceutically acceptable salt of the compound of formula (1).

8. The process according to claim 7, wherein the acid is hydrochloric acid, and the pharmaceutically acceptable salt of the compound of formula (1) is trihydrochloride salt of the compound of formula (1).

9. The process according to claim 8, comprising the step of recrystallizing the trihydrochloride salt of the compound of formula (1) with water and acetone.

* * * * *